US006905676B2

(12) United States Patent
Proost et al.

(10) Patent No.: US 6,905,676 B2
(45) Date of Patent: Jun. 14, 2005

(54) AMINO-TERMINALLY TRUNCATED MCP-2 AS CHEMOKINE ANTAGONISTS

(75) Inventors: Paul Proost, Heverlee-Leuven (BE); Sofie Struyf, Rumst (BE); Jo Van Damme, Brussels (BE)

(73) Assignee: Applied Research Systems ARS Holding N.V., Curacao (AN)

(*) Notice: Subject to any disclaimer, the term of this patent is extended or adjusted under 35 U.S.C. 154(b) by 0 days.

(21) Appl. No.: 09/537,859

(22) Filed: Mar. 28, 2000

(65) Prior Publication Data

US 2003/0124677 A1 Jul. 3, 2003

Related U.S. Application Data

(63) Continuation of application No. PCT/EP98/06142, filed on Sep. 28, 1998.

(30) Foreign Application Priority Data

Sep. 29, 1997 (EP) .............................. 97116863
Dec. 19, 1997 (EP) .............................. 97122471
Mar. 10, 1998 (EP) .............................. 98104216

(51) Int. Cl.[7] ........................ A61K 38/19; C07K 14/52
(52) U.S. Cl. ..................................... 424/85.1; 530/324
(58) Field of Search .............................. 530/350, 351; 44/85.1

(56) References Cited

U.S. PATENT DOCUMENTS 5,739,103 A  *  4/1998  Rollins et al.

FOREIGN PATENT DOCUMENTS

WO     WO 97/25427     7/1997

OTHER PUBLICATIONS

Proost et al. J. Immunol. Apr. 1998; 160:4034–4041.*
Sozzani et al., *Journal of Immunology*, pp. 3615–3622 (1994).
Proudfoot et al., *Journal of Biological Chemistry*, 271(5):2599–2603 (1996).
Proost et al., *Biochemistry*, 32:10170–10177 (1993).
Proost et al., *Journal of Immunology*, 150(3):1000–1010 (1993).
Proost et al., *METHODS: A Companion to Methods in Enzymology*, 10:82–92 (1996).
Proost et al., *Cytokine*, 7(2):97–104 (1995).
Grynkiewicz et al., *Journal of Biological Chemistry*, 260(6):3440–3450 (1995).
De Meester et al., *Journal of Immunological Methods*, 189:99–105 (1996).
Clark–Lewis et al., *Journal of Biological Chemistry*, 266(34):23128–23134 (1991).
Chang et al., *International Immunology*, 1(4):388–397 (1989).
Baggiolini et al., *Advances in Immunology*, 55:97–179, (1994).
Van Damme, et al., *J. Exp. Med.*, 176:59–65 (1992).
Weber et al., *J. Exp. Med.*, 183:681–685 (1996).
Gong et al., *Journal of Biological Chemistry*, 271(18):10521–10527 (1996).
Gong et al., *J. Exp. Med.*, 181:631–640 (1995).
Van Damme et al., *Eur. J. Immunol.*, 20:2113–2118 (1990).
Van Damme et al., *Eur. J. Biochem.*, 181:337–344 (1989).
Van Coillie et al., *Biochemical and Biophysical Research Communications*, 231:726–730 (1997).
Baggiolini et al., *Annual Review of Immunology*, 15:675–705 (1997).
Zhang et al., *Journal of Biological Chemistry*, 269(22):15918–15924 (1994).
Zhang et al., *METHODS: A Comparison To Methods in Enzymology*, 10:93–103 (1996).
Zhang et al., *Molecular and Cellular Biology*, 15(9):4851–4855 (1995).
Van Coillie et al., *Genomics*, 40:323–331 (1997).
Schols et al., *J. Exp. Med.*, 186(8):1383–1388 (1997).
Deng et al., *Nature*, 381:661–666 (1996).
Wuyts et al., *Biochemistry*, 36:2716–2723 (1997).
Taub., *Cytokine & Growth Factor Reviews*, 7(4):355–376 (1996).
Walz et al., *Biochemical and Biophysical Research Communications*, 159(3):969–975 (1989).

* cited by examiner

*Primary Examiner*—Prema Mertz
(74) *Attorney, Agent, or Firm*—Browdy and Neimark, P.L.L.C.

(57) ABSTRACT

The present invention relates to amino-terminally truncated MCP-2, lacking $NH_2$-terminal amino acids corresponding to amino acid residues 1, 1–2, 1–3, 1–4 or 1–5 of the naturally-occurring MCP-2 and having chemokine antagonistic activity, as well as cDNA sequences encoding them, their use in therapy and/or in diagnosis of the diseases, in which an antagonistic activity of the chemokine effects is required, and pharmaceutical compositions comprising them.

8 Claims, 3 Drawing Sheets

MCP-2

-23
MKVSAALLCL LLMAATFSPQ GLAQPDSVSI PITCCFNVIN RKIPIQRLES YTRITNIQCP
KEAVIFKTKR GKEVCADPKE RWVRDSMKHL DQIFQNLKP
                                        76

↓
1

MCP-2 Variant

-23
MKVSAALLCL LLMAATFSPQ GLAQPDSVSI PITCCFNVIN RKIPIQRLES YTRITNIQCP
KEAVIFQTKR GKEVCADPKE RWVRDSMKHL DQIFQNLKP
                                        76

AMINO-TERMINALLY TRUNCATED MCP-2 AS CHEMOKINE ANTAGONISTS

This application is a continuation of copending application International Application PCT/EP98/06142 filed on 28 Sep. 1998 and which designated the U.S.

FIELD OF THE INVENTION

The present invention relates to amino-terminally truncated MCP-2, lacking $NH_2$-terminal amino acids corresponding to amino acid residues 1, 1–2, 1–3, 1–4 or 1–5 of the naturally-occurring MCP-2 and having chemokine antagonistic activity, as well as cDNA sequences encoding them, their use in therapy and/or in diagnosis of the diseases, in which an antagonistic activity of the chemokine effects is required, and pharmaceutical compositions comprising them.

BACKGROUND OF THE INVENTION

Chemokines constitute a family of small pro-inflammatory cytokines with leukocyte chemotactic and activating properties. Depending on the position of the first cysteines, the chemokine family can be divided in C—C, C—X—C and C—$X_3$—C chemokines (Baggiolini M. et al., 1994; Baggiolini M. et al., 1997 and Taub D. et al., 1996).

Many C—X—C chemokines such as interleukin-8 (IL-8) are chemotactic for neutrophils, while C—C chemokines, such as monocyte chemotactic protein-3 (MCP-3), are active on a variety of leukocytes including monocytes, lymphocytes, eosinophils, basophils, NK cells and dendritic cells.

The $NH_2$-terminal domain of chemokines is involved in receptor-binding and $NH_2$-terminal processing can either activate chemokines or render chemokines completely inactive.

The C—X—C chemokine platelet basic protein becomes a neutrophil chemotactic peptide (NAP-2) only after removal of the 24 $NH_2$-terminal residues (Walz A. et al., 1989 and Van Damme J. et al., 1990).

Deletion of up to 8 $NH_2$-terminal residues from IL-8 results in an enhanced chemotactic activity, but further cleavage of the Glu-Leu-Arg motif, which is located in front of the first Cys in all neutrophil chemotactic C—X—C chemokines, causes complete inactivation (Clark-Lewis I. et al., 1991).

Similar $NH_2$-terminal proteolysis (up to 8 amino acids) of another C—X—C chemokine, granulocyte chemotactic protein-2 (GCP-2), has no effect on the neutrophil chemotactic activity (Proost P. et al, 1993a).

The synthetical C—C chemokines MCP-1, MCP-3 and RANTES missing the 8 to 9 $NH_2$-terminal amino acids are inactive on monocytes and are useful as receptor antagonists (Gong J. et al., 1996; and Gong J. et al., 1995).

Extension of RANTES with one methionine results in complete inactivation of the molecule and Met-RANTES behaves as an antagonist for the authentic RANTES (Proudfoot A. E. et al., 1996).

The clone of human MCP-2 (Monocyte Chemoattractant Protein-2) has been isolated by differential library screening with cDNA probes derived from stimulated versus resting peripheral blood lymphocytes (PBL) (it was initially called "HC14", Chang H. C. et al., 1989). The cDNA-derived protein sequence was identical to that of purified natural MCP-2; however, a putative allelic variant has also been isolated, in which Gln 46 replaces Lys 46 (Van Coillie et al., 1997).

MCP-2 has also been synthesized by solid-phase chemistry (Proost P. et al., 1995).

DESCRIPTION OF THE INVENTION

The main object of the present invention are amino-terminally truncated MCP-2, lacking $NH_2$-terminal amino acids corresponding to amino acid residues 1, 1–2, 1–3, 1–4 or 1–5 of the naturally-occurring MCP-2 and having chemokine antagonistic activity More particularly, one object of the present invention is MCP-2 (6–76), which is MCP-2 lacking the 1–5 $NH_2$-terminal amino acids, as shown in FIG. 1 and in SEQ ID NO: 3 or SEQ ID NO: 4.

Such amino-terminally truncated MCP-2 of the invention can be in a glycosylated or non-glycosylated form.

The term "chemokine antagonist" means 'which acts as antagonist to the mature full-length naturally-occurring chemokines'.

Another object of the invention are the DNA molecules comprising the DNA sequences coding for the amino-terminally truncated MCP-2 of the invention, including nucleotide sequences substantially the same.

"Nucleotide sequences substantially the same" includes all other nucleic acid sequences which, by virtue of the degeneracy of the genetic code, also code for the given amino acid sequences.

The invention also includes expression vectors which comprise the above DNAs, host-cells transformed with such vectors and a process of preparation of such amino-terminally truncated MCP-2 of the invention, through the culture in appropriate culture media of said transformed cells.

The DNA sequence coding for the proteins of the invention can be inserted and ligated into a suitable plasmid. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art (see Sambrook et al, 1989). Double stranded cDNA is linked to plasmid vectors by homopolymeric tailing or by restriction linking involving the use of synthetic DNA linkers or blunt-ended ligation techniques: DNA ligases are used to ligate the DNA molecules and undesirable joining is avoided by treatment with alkaline phosphatase.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector(s), having the operably linked transcriptional and translational regulatory signals, which is capable of integrating the desired gene sequences into the host cell.

The cells which have been stably transformed by the introduced DNA can be selected by also introducing one or more markers which allow for selection of host cells which contain the expression vector. The marker may also provide for phototrophy to a auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese hamster ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

The amino-terminally truncated MCP-2 of the invention may be prepared by any other well known procedure in the art, in particular, by the well established chemical synthesis procedures, utilizing automated solid-phase peptide synthesizers followed by chromatographic purification.

The chemokines of the invention may, for example, be synthesized by Fmoc (9-fluorenylmethoxycarbonyl), tBoc (t-butoxycarbonyl) or any other comparable chemical synthesis with or without appropriate side-chain protection groups on the different amino acids. The amino acids with or without appropriate side-chain protection groups are preactivated—e.g. with HBTU/HOBt [2-(1H-Benzotriazole-1yl)-1,1,3,3-tetramethyl-uromium hexafluorophosphate/1-hydroxybenzotriazole)—and coupled to the growing peptide chain. Before the addition of the following residue, the protection group (e.g. Fmoc) is removed from the α-amino group. After synthesis, all protection groups are removed, the intact full length peptides are purified and chemically or enzymatically folded (including the formation of disulphide bridges between cysteines) into the corresponding chemokines of the invention.

Purification of the natural, synthetic or recombinant proteins is carried out by any one of the methods known for this purpose, i.e. any conventional procedure involving extraction, precipitation, chromatography, electrophoresis, or the like (see for example Proost P. et al., 1996). A further purification procedure that may be used in preference for purifying the protein of the invention is affinity chromatography using monoclonal antibodies, or affinity for heparin, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength.

The amino-terminally truncated MCP-2 of the invention are useful in the therapy and/or diagnosis of the diseases, in which an antagonistic activity of the chemokine effects is required. Examples of such diseases include: inflammatory diseases, angiogenesis- and hematopoiesis-related diseases, tumors, infectious diseases, including HIV, auto-immune diseases, atherosclerosis, pulmonary diseases and skin disorders.

Therefore, in a further aspect, the present invention provides the use of the protein of the invention in the manufacture of a medicament for the treatment of the above-mentioned diseases.

The medicament is preferably presented in the form of a pharmaceutical composition comprising the proteins of the invention together with one or more pharmaceutically acceptable carriers and/or excipients. Such pharmaceutical compositions form yet a further aspect of the present invention.

A further embodiment of the invention is the method of treatment of the above-mentioned diseases comprising administering a pharmacologically active amount of the amino-terminally truncated MCP-2 of the invention to subjects at risk of developing such diseases or to subjects already showing such pathologies.

The invention will now be described by means of the following Examples, which should not be construed as in any way limiting the present invention. The Examples will refer to the Figures specified here below.

DESCRIPTION OF THE FIGURES

FIG. 1 shows the amino acid sequence of MCP-2 (SEQ ID NO: 1) and of its known variant (SEQ ID NO: 2). Signal sequences are reported in italics, whereas C-residues are in bold. Arrows indicate the first amino acids of the amino-terminally truncated MCP-2(6–76) of the invention. Underlined is the amino acid, which is different in the MCP-2 variant.

lane 3: natural MCP-2 (6–76, 30 ng/lane); and
lane 4: synthetic MCP-2 (1–76, 60 ng/lane).
Gels were run under reducing conditions and proteins were stained with silver.

Figure 3:
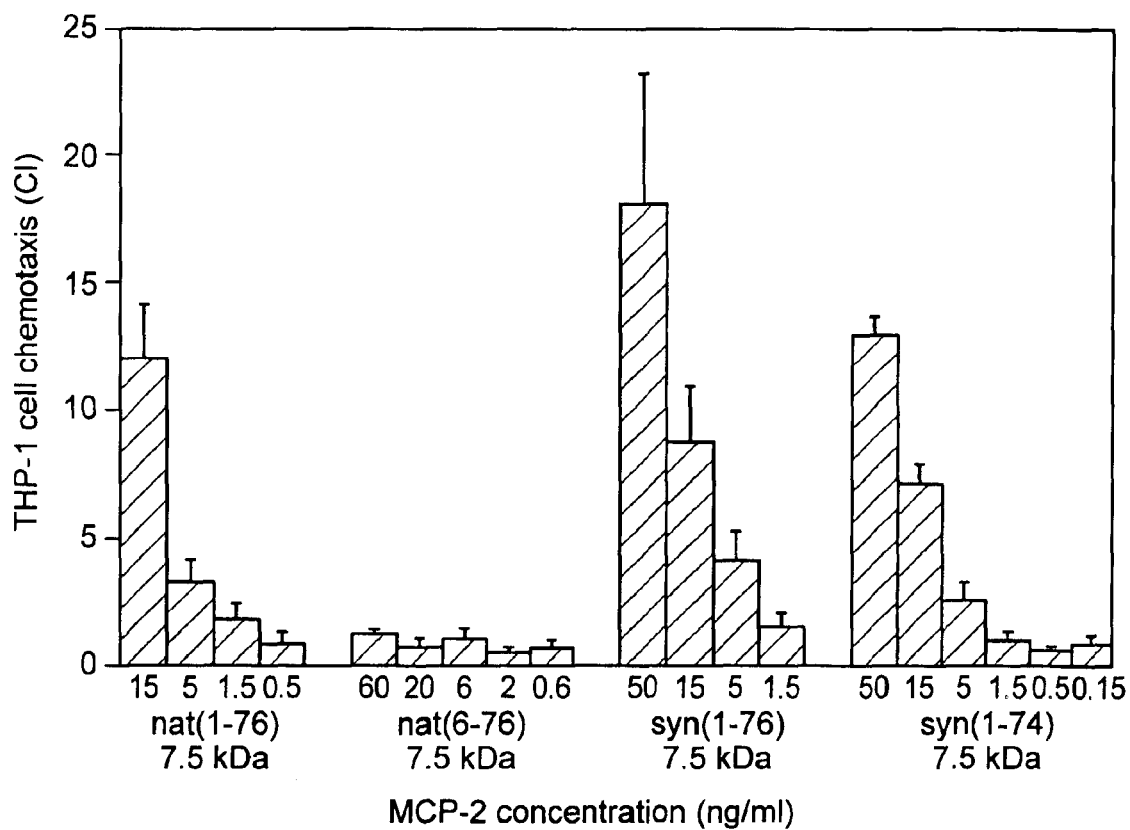

FIG. 3: it shows a comparison of the chemotactic potency of modified MCP-2 forms. Intact natural (nat) and synthetic (syn) MCP-2(1–76), $NH_2$-terminally truncated natural MCP-2(6–76) and COOH-terminally truncated synthetic MCP-2(1–74) were tested for chemotactic activity on THP-1 cells. Results represent the mean CI±SEM from four or more independent experiments.

Figure 4A:
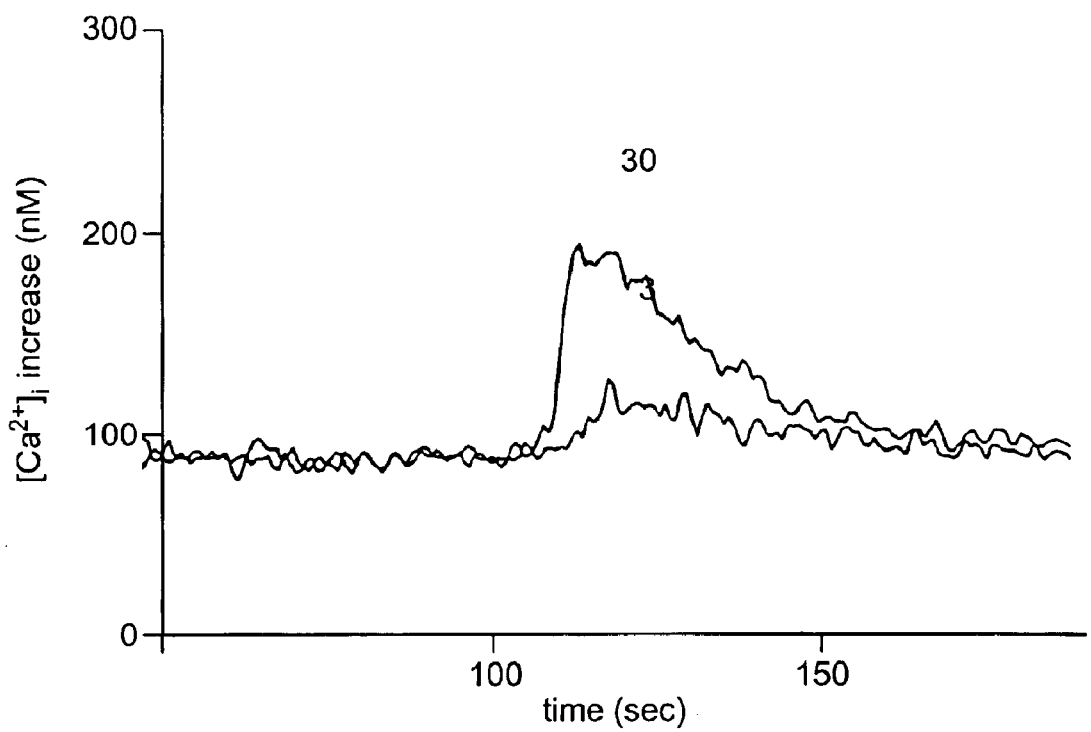
Figure 4B:
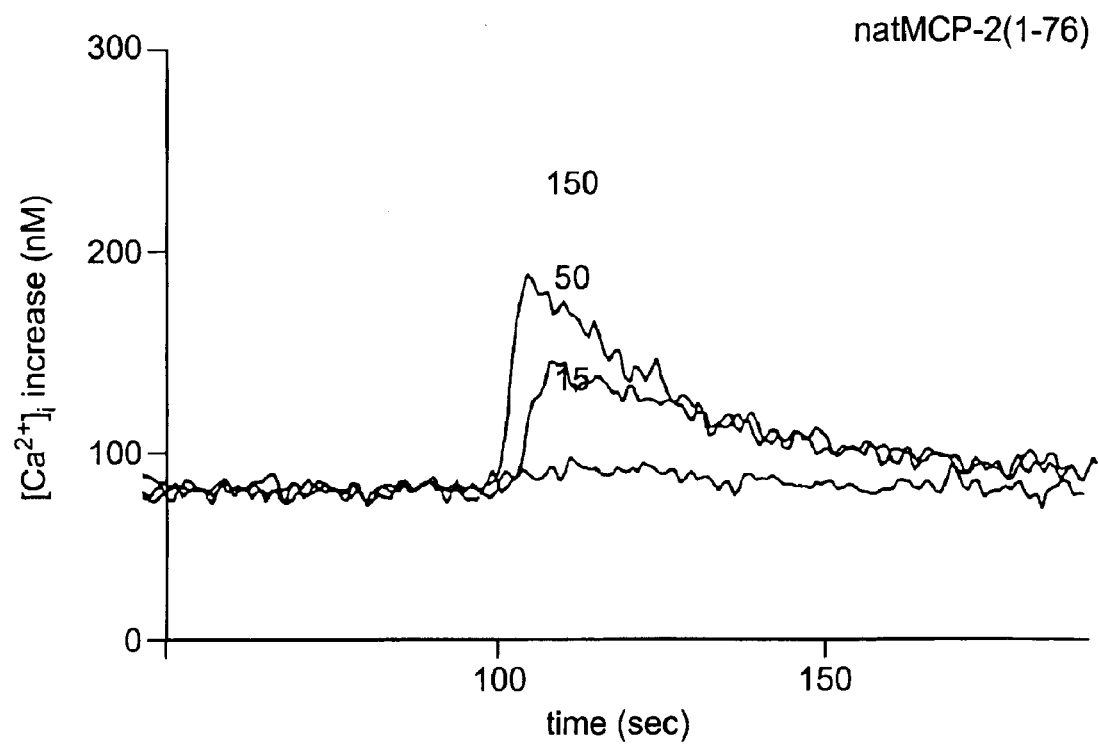

FIGS. 4A+4B: Natural MCP-2 (FIG. 4B) is a weaker agonist than MCP-1 (FIG. 4A) to mobilize calcium and monocytes. Intact MCP-2 (15, 50 and 150 ng/ml) dose-dependently increases the $[Ca^{2+}]i$ in THP-1 cells. The result of one representative experiment out of two is shown.

EXAMPLES

Example 1

Amino-Terminally Truncated MCP-2

Materials and Methods
Chemokine and Immunoassay

MCP-2 was synthesized and purified as described earlier (Proost P. et al., 1995).

Specific anti-human MCP-2 Ab were obtained from mice and affinity purified on a Sepharose column to which synthetic MCP-2 was coupled using the conditions provided by the manufacturer (CNBr activated Sepharose 4B, Pharmacia, Uppsala, Sweden).

ELISA plates were coated with the affinity purified anti-human MCP-2 and biotinylated anti-MCP-2 was used as the capturing Ab. The detection was performed with peroxidase labeled streptavidine and TMB. The detection limit for the MCP-2 ELISA was about 0.1 ng/ml.

Production and Purification of MCP-2

Monocyte chemotactic proteins were purified from peripheral blood mononuclear cell-derived conditioned medium from 132 blood donations obtained from Blood Transfusion Centers of Antwerp and Leuven (Proost P. et al., 1996).

Erythrocytes and granulocytes were removed by sedimentation in hydroxyethyl starch (Fresenius A G, Bad Homburg, Germany) and by gradient centrifugation in a sodium metrizoate solution (Lymphoprep; Nyegaard, Oslo Norway).

Mononuclear cells ($60 \times 10^9$ cells) were incubated ($5 \times 10^6$ cells/ml) with 10 µg/ml Con A and 2 µg/ml of LPS. After 48 to 120 h, conditioned medium was collected and kept at $-20°$ C. until purification.

Natural MCP-2 was purified in a four step purification procedure as previously described (Proost P. et al., 1996).

Briefly, the conditioned medium was concentrated on controlled pore glass or silicic acid and partially purified by affinity chromatography on a heparin-Sepharose column (Pharmacia).

Fractions containing MCP-2 immunoreactivity were further purified by Mono S (Pharmacia) cation exchange chromatography and eluted in a NaCl gradient at pH 4.0.

Natural MCP-2 were purified to homogeneity through RP-HPLC on a C-8 Aquapore RP-300 column (Perkin Elmer, Norwalk Conn.) equilibrated with 0.1% trifluoroacetic acid TFA). Proteins were eluted in an acetonitrile gradient.

Biochemical Characterization of MCP-Forms by SDS-PAGE, Amino Acid Sequence Analysis and Mass Spectrometry The purity of column fractions was examined by SDS-PAGE under reducing conditions on Tris/tricine gels (Proost P. et al., 1996). Proteins were stained with silver and the following relative molecular (Mr) markers were used: OVA (Mr 45,000), carbonic anhydrase (Mr 31,000), soybean trypsin inhibitor (Mr 21,500), β-lactoglobulin (Mr 18,400), lysozyme (Mr 14,400) and aprotinin (Mr 6,500).

The $NH_2$-terminal sequence of purified chemokines was determined by Edman degradation on a pulsed liquid 477A/120A protein sequencer (Perkin Elmer) with N-methylpiperidine as a coupling base. Blocked proteins were cleaved between Asp and Pro in 75% formic acid for 50 h. The formic acid digest was sequenced without further purification.

The Mr of MCP-2 was determined by matrix-assisted laser desorption ionization/time of flight-mass spectrometry (MALDI/TOF-MS) (Micromass TofSpec, Manchester, UK). Alpha-cyano4-hydroxycinnamic acid and cytochrome C were used as matrix and internal standard, respectively.

Detection of Chemotactic Activity

MCP-2 was tested for its chemotactic potency on freshly purified monocytes ($2 \times 10^6$ cells/ml) or monocytic THP-1 cells ($0.5 \times 10^6$ cells/ml; 2 days after subcultivation) in the Boyden microchamber using polyvinylpyrrolidone-treated polycarbonate membranes with 5 µm pore size.

Samples and cells were diluted in HBSS (Life technologies/Gibco BRL, Paisley, Scotland) supplemented with 1 mg/ml human serum albumin (Red Cross Belgium). After 2 h incubation at 37° C., the cells were fixed and stained with Diff-Quick staining solutions (Harleco, Gibbstown. N.J.) and the cells that migrated through the membranes were counted microscopically in ten oil immersion fields at 500-fold magnification.

The chemotactic index (CI) of a sample (triplicates in each chamber) was calculated as the number of cells that migrated to the sample over the number of cells that migrated to control medium (Van Damme J. et al., 1992).

For desensitization experiments, cells were incubated with biologically inactive chemokine-variants for 10 min. at 37° C., before they were added to the upper well of the Boyden microchamber. The % inhibition of the CI was calculated using the CI from HBSS treated cells towards the sample as a reference value.

Detection of Intracellular $Ca^{2+}$ Concentrations

Intracellular calcium concentrations ($[Ca^{2+}]_i$) were measured as previously described (Wuyts A. et al., 1997). Purified monocytes or THP-1 cells ($10^7$ cells/ml) were incubated in Eagle's Minimum Essential Medium (EMEM, Gibco)+0.5% FCS with the fluorescent indicator fura-2 (fura-2/AM 2.5 µM; Molecular Probes Europe BV, Leiden, The Netherlands) and 0.01% Pluronic F-127 (Sigma, St Louis Mo.).

After 30 min at 37° C. the cells were washed twice and resuspended at $10^6$ cells/ml in HBSS with 1 mM $Ca^{2+}$ and 0.1% FCS (buffered with 10 mM Hepes/NaOH at pH 7.4). The cells were equilibrated at 37° C. for 10 min before fura-2 fluorescence was measured in a LS50B luminescence spectrophotometer (Perkin Elmer).

Upon excitation at 340 and 380 nm, fluorescence was detected at 510 run. The $[Ca^{2+}]_i$ was calculated from the Grynkiewicz equation (Grynkiewicz et al, 1985). In order to determine $R_{max}$ the cells were lysed with 50 µM digitonin. Subsequently, the pH was adjusted to 8.5 with 20 mM Tris and $R_{min}$ was obtained by addition of 10 mM EGTA to the lysed cells. The $K_d$ used was 224 nM.

For desensitization experiments, monocytes or THP-1 cells were first stimulated with buffer, chemokine or chemokine antagonist at different concentrations. As a second stimulus, MCP-2 was used at a concentration inducing a significant increase in the $[Ca^{2+}]_i$ after prestimulation with buffer. The second stimulus was applied 2 min after addition of the first stimulus. The percentage inhibition of the $[Ca^{2+}]_i$ increase in response to the second stimulus was calculated comparing the signal after prestimulation with chemokine or chemokine antagonist with the signal after addition of buffer.

Results

Isolation of Post-Translationally Modified MCP-2 Forms

A specific and sensitive ELISA was used to trace different MCP-2 forms produced by peripheral blood mononuclear cells stimulated with mitogen and endotoxin.

The conditioned medium was purified according to a standard isolation procedure (Proost P. et al., 1996), including adsorption to controlled pore glass and heparin Sepharose chromatography.

Subsequently, purification by FPLC mono S cation exchange chromatography was carried out and then a further purification step with C-8 RP HPLC was applied. Molecular masses were measured by SDS-PAGE and by MALDI/TOF-MS.

Figure 2:
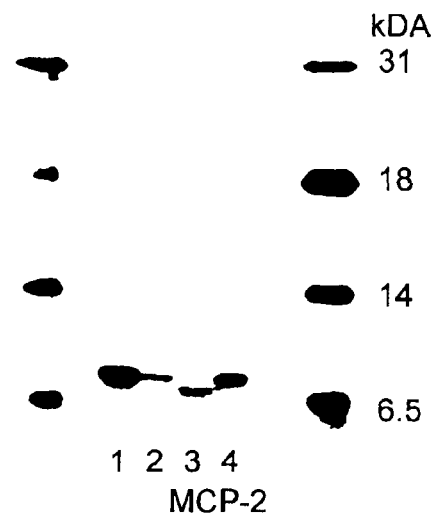
FIG. 2: SDS-PAGE of amino-terminally truncated MCP-2(6–76):
lane 1: natural MCP-2 (1–76, 100 ng/lane):
lane 2: natural MCP-2 (1–76, 30 ng/lane)

Different forms of MCP-2 were isolated: in addition to the authentic 7.5 kDa MCP-2(1–76), an $NH_2$-terminally truncated 7 kDa form of MCP-2 missing five residues [MCP-2 (6–76)] was purified to homogeneity by RP-HPLC and identified by amino acid sequence analysis (FIG. 2). MALDI/TOF-MS (Table I) yielded a molecular mass of 8881 Da for intact MCP-2 (theoretical Mr of 8893 Da), whereas for the MCP-2(6–76) a molecular mass of 8365 Da was measured, confirming the deletion of the five $NH_2$-terminal amino acids (theoretical Mr of 8384 Da). Functional comparison of these natural MCP-2 forms in the THP-1 chemotaxis assay showed that intact MCP 2 is still active at 5 ng/ml, whereas truncated MCP-2(6–76) remains devoid of chemotactic activity when tested at a concentration range from 0.6 to 60 ng/ml (FIG. 3). Intact natural MCP-2 was also compared in potency with the synthetical MCP-2(1–76) and a COOH-terminally truncated synthetical form (Proost P. et al., 1995) missing two residues [MCP-2 (1–74)].

The minimal effective chemotactic concentration of these forms was also found to be 5 ng/ml (FIG. 3). Although in chemotaxis assays the specific activity of natural intact MCP-1 and MCP-2 is comparable (Van Damme J, et al., 1992), the calcium mobilizing capacity of MCP-2 is still a matter of debate.

However, in $Ca^{2+}$-mobilization experiments, the minimal effective dose for both natural or synthetic MCP-2(1–76) was 10-fold higher compared to that of natural intact MCP-1(1–76) (FIG. 4), whereas MCP-2(6–76) remained inactive.

Nevertheless, intact MCP-2 (50 ng/ml) was capable to desensitize for MCP-2 (15 ng/ml) and MCP-3 (10 ng/ml) yielding 52% and 45% inhibition of chemotaxis, respectively.

Due to this lower specific activity of MCP-2 in $Ca^{2+}$ assays, desensitization of chemotaxis by MCP-2(6–76) was performed in the Boyden microchamber. Since intact MCP-2 is reported to cross-desensitize with active MCP-1, MCP-2 and MCP 3 in the monocyte chemotaxis assay (Sozzani S. et al., 1994), we investigated whether natural, inactive MCP-2(6–76) could also desensitize for MCP-1, MCP-2, MCP-3 and RANTES (Table II). Pre-incubation of THP-1 cells with 100 ng/ml of inactive MCP-2(6–76) could already significantly inhibit chemotaxis induced by 10 ng/ml of MCP-1 (63%), 5 ng/ml of MCP-2 (75%), 30 ng/ml of MCP-3 (62%) and 100 ng/ml of RANTES (75%). Moreover, chemotaxis in response to 3 times lower concentrations of the respective MCPs was completely (91–100%) inhibited by 100 ng/ml MCP-2(6–76). Furthermore, at a concentration as low as 10 ng/ml, MCP-2(6–76) was still able to significantly inhibit the chemotactic activity induced by MCP-1 (3 ng/ml), MCP-2 (1.5 ng/ml) or MCP 3 (10 ng/ml) and RANTES (30 ng/ml). Taken together, MCP-2(6–76) is produced naturally, is inactive as a chemoattractant and antagonizes several C—C chemokines, the effect being most predominant for MCP-3.

TABLE I

Biochemical characterization of natural forms of MCP-2.
$NH_2$-terminal amino acid sequence analysis and comparison of the experimental (SDS-PAGE and MALDI/TOF-MS) and theoretical Mr of C-8 RP-HPLC purified natural MCP-isoforms.

| MCP-form | $NH_2$-terminal sequence | Mr (Da) theoretical unglycosylated | SDS-PAGE | MALDI/TOF-MS |
|---|---|---|---|---|
| MCP-2 (1-76) | blocked | 8893 | 7500 | 8881 |
| MCP-2 (2-76) | SIPITCC (residues 6–12 of the mature portion of SEQ ID NOS 1 & 2, or residues 1–7 of SEQ ID NOS 3 & 4) | 8384 | 7000 | 8365 |

TABLE II

MCP-2(6–76) desensitizes the monocyte chemotactic responses of MCP-1, MCP-2 MCP-3 and RANTES in the microchamber.

| Chemokine[a] | Concentration | Antagonization of chemotactic response[b,c] | | % Inhibition of chemotaxis |
|---|---|---|---|---|
| | | buffer | 100 ng/ml MCP-2(6–76) | |
| MCP-1 | 10 | 22.3 ± 7.9 | 8.3 ± 3.8 | 63 ± 21 |
|  | 3 | 15.0 ± 8.0 | 1.3 ± 0.3 | 99 ± 1.0 |
| MCP-2 | 5 | 36.0 ± 12.6 | 10.8 ± 6.1 | 75 ± 8.0 |
|  | 1.5 | 6.7 ± 1.4 | 1.5 ± 0.3 | 91 ± 7.0 |
| MCP-3 | 30 | 13.2 ± 0.4 | 6.0 ± 4.0 | 62 ± 31 |
|  | 10 | 3.0 ± 1.5 | <1 | 100 ± 0.0 |

TABLE II-continued

MCP-2(6–76) desensitizes the monocyte chemotactic responses of MCP-1, MCP-2 MCP-3 and RANTES in the microchamber.

| Chemokine[a] | Concentration | Antagonization of chemotactic response[b,c] | | % Inhibition of chemotaxis |
|---|---|---|---|---|
| | | buffer | 100 ng/ml MCP-2(6–76) | |
| RANTES | 100 | 6.3 ± 0.8 | 2.6 ± 1.3 | 75 ± 19 |
| | 30 | 4.0 ± 0.8 | 1.5 ± 0.3 | 77 ± 16 |
| | | buffer | 10 ng/ml MCP-2(6–76) | |
| MCP-1 | 10 | 12.7 ± 2.3 | 10.5 ± 3.8 | 24 ± 1.8 |
| | 3 | 7.5 ± 0.0 | 3.0 ± 0.3 | 69 ± 4.0 |
| MCP-2 | 5 | 38.0 ± 5.3 | 27.2 ± 4.9 | 30 ± 6.0 |
| | 1.5 | 18.3 ± 4.6 | 9.2 ± 1.4 | 45 ± 23 |
| MCP-3 | 30 | 13.2 ± 1.9 | 8.0 ± 1.0 | 37 ± 19 |
| | 10 | 7.7 ± 1.4 | 1.7 ± 0.3 | 90 ± 6.0 |
| RANTES | 100 | 5.5 ± 0.6 | 5.8 ± 0.9 | 17 ± 7.0 |
| | 30 | 3.2 ± 0.7 | 2.5 ± 0.5 | 39 ± 18 |

[a]MCP-1, MCP-2, MCP-3 or RANTES were added as chemoattractants to the lower wells.
[b]the upper wells of the microchamber were filled with THP-1 cells preincubated with MCP-2(6–76) or with buffer
[c]mean CI ± SEM of 3 independent experiments References Baggiolini M. et al., *Ann. Rev. Immunol.,* 55, 97–179, 1994.
Baggiolini M. et al.,*Ann. Rev. Immunol.,* 15, 675–705, 1997.
Chang H. C. et al., *International Immunology,* 1(4), 388–397, 1989.
Clark-Lewis I. et al., *J. Biol. Chem.,* 266, 23128–23134, 1991.
De Meester I. et al., *J. Immunol. Methods* 189, 99–10526, 1996.
Deng H. et al., *Nature.,* 381, 661–666, 1996.
Gong J. et al. *J. Exp. Med.,* 181, 631–640, 1995.
Gong J. et al., *J. Biol. Chem.* 271, 10521–10527, 1996.
Grynkiewicz G. et al., *J. Biol. Chem.,* 260, 3440, 1985.
Proost P. et al., *Biochemistry,* 32, 10170–10177, 1993a.
Proost P. et al., *J. Immunol.,* 150, 1000–1010, 1993.
Proost P. et al., *Cytokine,* 7, 97–104, 1995.
Proost P. et al., *Methods: A companion to Methods in Enzymol.,* 10, 82, 1996.
Proudfoot A. E. et al.,*J. Biol. Chem.,* 271, 2599–2603, 1996.
Sambrook et al., Molecular Cloning: A laboratory Manual, Cold Spring Harbor Laboratory, Cold Spring Harbor, N.Y., 1989.
Schols D. et al., *J. Exp. Med.,* 186, 1383–1388, 1997.
Sozzani S. et al., *J. Immunol.,* 152, 3615, 1994.
Taub D. et al., *Cytokine & Growth Factor Reviews,* 7, 335–76, 1996.
Van Coillie E. et al., *Biochem. Biophys. Res. Commun.,* 231, 726–730, 1997.
Van Dammne J. et al., Eur. J. Biochem., 181, 337–344, 1989.
Van Damme J. et al., *Eur. J. Immunol.,* 20, 2113–8, 1990.
Van Damme J. et al., *J. Exp. Med.,* 176, 59, 1992.
Walz A. et al., *Biochem. Biophys. Res. Commun.,* 159, 969–75, 1989.
Wuyts A., et al., *Biochemistry* 36, 2716–2723, 1997.

What is claimed is:

1. An isolated amino-terminally truncated MCP-2 polypeptide consisting of residues 2–76 of SEQ ID NO:2, wherein the truncated MCP-2 polypeptide lacks $NH_2$-terminal amino acid residue 1 of SEQ ID NO:2 and has chemokine antagonistic activity.

2. An isolated amino-terminally truncated MCP-2 polypeptide consisting of residues 3–76 of SEQ ID NO:2, wherein the truncated MCP-2 polypeptide lacks $NH_2$-terminal amino acid residues 1–2 of SEQ ID NO:2 and has chemokine antagonistic activity.

3. An isolated amino-terminally truncated MCP-2 polypeptide consisting of residues 4–76 of SEQ ID NO:2, wherein the truncated MCP-2 polypeptide lacks NH2-terminal amino acid residues 1–3 of SEQ ID NO:2 and has chemokine antagonistic activity.

4. An isolated amino-terminally truncated MCP-2 polypeptide consisting of residues 5–76 of SEQ ID NO:2, wherein the truncated MCP-2 polypeptide lacks $NH_2$-terminal amino acid residues 1–4 of SEQ ID NO:2 and has chemokine antagonistic activity.

5. An isolated amino-terminally truncated MCP-2 polypeptide consisting of residues 6–76 of SEQ ID NO:2, wherein the truncated MCP-2 polypeptide lacks $NH_2$-terminal amino acid residues 1–5 of SEQ ID NO:2 and has chemokine antagonistic activity.

6. The isolated amino-terminally truncated MCP-2 polypeptide of any one of claims 1–4 and 5, wherein the truncated MCP-2 polypeptide is in glycosylated form.

7. A pharmaceutical composition comprising an isolated truncated MCP-2 polypeptide according to any one of claims 1–4 and 5, wherein the composition comprises one or more pharmaceutically acceptable carriers and/or excipients.

8. The pharmaceutical composition according to claim 7, wherein the isolated truncated MCP-2 polypeptide is in glycosylated form.

* * * * *

SEQUENCE LISTING

<160> NUMBER OF SEQ ID NOS: 4

<210> SEQ ID NO 1
<211> LENGTH: 99
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Met Lys Val Ser Ala Ala Leu Leu Cys Leu Leu Leu Met Ala Ala Thr
 1               5                  10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
        35                  40                  45

Glu Ser Tyr Thr Arg Ile Thr Asn Ile Gln Cys Pro Lys Glu Ala Val
    50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 2
<211> LENGTH: 99
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 2

Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
        35                  40                  45

Glu Ser Tyr Thr Arg Ile Thr Asn Ile Gln Cys Pro Lys Glu Ala Val
50                  55                  60

Ile Phe Lys Thr Gln Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 3
<211> LENGTH: 71
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Pro Ile Thr Cys Cys Phe Asn Val Ile Asn Arg Lys Ile Pro
1               5                   10                  15

Ile Gln Arg Leu Glu Ser Tyr Thr Arg Ile Thr Asn Ile Gln Cys Pro
            20                  25                  30

Lys Glu Ala Val Ile Phe Lys Thr Lys Arg Gly Lys Glu Val Cys Ala
        35                  40                  45

Asp Pro Lys Glu Arg Trp Val Arg Asp Ser Met Lys His Leu Asp Gln
50                  55                  60

Ile Phe Gln Asn Leu Lys Pro
65                  70

<210> SEQ ID NO 4
<211> LENGTH: 71
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ile Pro Ile Thr Cys Cys Phe Asn Val Ile Asn Arg Lys Ile Pro
1               5                   10                  15

Ile Gln Arg Leu Glu Ser Tyr Thr Arg Ile Thr Asn Ile Gln Cys Pro
            20                  25                  30

Lys Glu Ala Val Ile Phe Lys Thr Gln Arg Gly Lys Glu Val Cys Ala
        35                  40                  45

Asp Pro Lys Glu Arg Trp Val Arg Asp Ser Met Lys His Leu Asp Gln
50                  55                  60

Ile Phe Gln Asn Leu Lys Pro
65                  70
```